(12) United States Patent
Garcia

(10) Patent No.: US 10,058,364 B2
(45) Date of Patent: Aug. 28, 2018

(54) LOCKING MECHANISM TO SECURE ENDS OF AN IMPLANTABLE BAND

(75) Inventor: Saddy R. Garcia, St. Augustine, FL (US)

(73) Assignee: Zimmer Biomet CMF and Thoracic, LLC, Jacksonville, FL (US)

( * ) Notice: Subject to any disclaimer, the term of this patent is extended or adjusted under 35 U.S.C. 154(b) by 590 days.

(21) Appl. No.: 14/128,862

(22) PCT Filed: Jun. 29, 2012

(86) PCT No.: PCT/US2012/044920
§ 371 (c)(1),
(2), (4) Date: Apr. 4, 2014

(87) PCT Pub. No.: WO2013/003719
PCT Pub. Date: Jan. 3, 2013

(65) Prior Publication Data
US 2014/0378976 A1 Dec. 25, 2014

Related U.S. Application Data

(60) Provisional application No. 61/502,615, filed on Jun. 29, 2011.

(51) Int. Cl.
*A61B 17/82* (2006.01)
*A61B 17/84* (2006.01)
*A61B 17/80* (2006.01)

(52) U.S. Cl.
CPC .......... *A61B 17/823* (2013.01); *A61B 17/842* (2013.01); *A61B 17/80* (2013.01); *A61B 17/8076* (2013.01)

(58) Field of Classification Search
CPC ....... A61B 17/82; A61B 17/84; A61B 17/823; A61B 17/842
USPC .......................................................... 606/74
See application file for complete search history.

(56) References Cited

U.S. PATENT DOCUMENTS

| | | |
|---|---|---|
| 1,962,964 A | 6/1934 | Morrison |
| 2,226,393 A | 12/1940 | Seeger et al. |
| 2,443,335 A | 6/1948 | Vogel |
| 3,045,306 A | 7/1962 | Taylor |
| 4,371,192 A | 2/1983 | Alix |

(Continued)

FOREIGN PATENT DOCUMENTS

| | | |
|---|---|---|
| EP | 2725998 B1 | 8/2016 |
| FR | 2900561 A1 | 11/2007 |
| WO | WO2013003719 A1 | 1/2013 |

OTHER PUBLICATIONS

"European Application Serial No. 12804228.0, Extended European Search Report dated Oct. 22, 2014", 8 pgs.

(Continued)

*Primary Examiner* — Christopher Beccia
(74) *Attorney, Agent, or Firm* — Schwegman Lundberg & Woessner, P.A.

(57) ABSTRACT

A locking mechanism for securing ends of an implantable fabric including a plate member having an aperture therethrough. A cam member is rotatable relative to the aperture between a locked state and an unlocked state. The implantable fabric is movable relative to the plate member when the cam member is in the unlocked state and restricted from moving relative to the plate member when the cam member is in the locked state.

27 Claims, 11 Drawing Sheets

(56) References Cited

U.S. PATENT DOCUMENTS

| | | | |
|---|---|---|---|
| 5,070,805 A | 12/1991 | Plante | |
| 5,190,545 A * | 3/1993 | Corsi | A61B 17/82 606/309 |
| 5,335,400 A | 8/1994 | Sales | |
| 5,356,412 A | 10/1994 | Golds et al. | |
| 5,383,905 A | 1/1995 | Golds et al. | |
| 5,415,658 A | 5/1995 | Kilpela et al. | |
| 5,423,821 A | 6/1995 | Pasque | |
| 6,015,428 A | 1/2000 | Pagedas | |
| 6,017,347 A | 1/2000 | Huebner et al. | |
| 6,066,160 A | 5/2000 | Colvin et al. | |
| 6,086,608 A | 7/2000 | Ek et al. | |
| 6,099,527 A * | 8/2000 | Hochschuler | A61B 17/8869 606/279 |
| 6,120,505 A | 9/2000 | Huebner | |
| 6,656,185 B2 * | 12/2003 | Gleason | A61B 17/82 24/135 R |
| 6,682,533 B1 * | 1/2004 | Dinsdale | A61B 17/82 24/134 P |
| 6,974,452 B1 | 12/2005 | Gille et al. | |
| 7,052,499 B2 | 5/2006 | Steger et al. | |
| 7,458,981 B2 | 12/2008 | Fielding et al. | |
| 7,803,176 B2 | 9/2010 | Teague et al. | |
| 8,172,887 B2 | 5/2012 | Gabele | |
| 8,579,901 B1 * | 11/2013 | Foerster | A61B 17/82 606/74 |
| 2006/0195104 A1 | 8/2006 | Schlafli et al. | |
| 2006/0217713 A1 | 9/2006 | Serhan et al. | |
| 2008/0140128 A1 | 6/2008 | Smisson et al. | |
| 2009/0105717 A1 * | 4/2009 | Bluechel | A61B 17/8061 606/280 |
| 2010/0094294 A1 | 4/2010 | Gillard et al. | |
| 2010/0179600 A1 | 7/2010 | Steger et al. | |
| 2011/0035008 A1 | 2/2011 | Williams | |
| 2012/0059377 A1 | 3/2012 | Belliard | |
| 2012/0130373 A1 | 5/2012 | Larroque-Lahitette | |
| 2012/0157998 A1 | 6/2012 | Belliard | |
| 2012/0215224 A1 | 8/2012 | Songer | |
| 2012/0303065 A1 * | 11/2012 | Larroque-Lahitette | A61B 17/7002 606/277 |

OTHER PUBLICATIONS

International Search Report regarding Application No. PCT/US2012/044920 dated Sep. 25, 2012.

Patentability Search Report, "Locking Mechanism to Secure the Ends of an Implantable Braid" dated Feb. 5, 2011.

Written Opinion regarding Application No. PCT/US2012/044920 dated Sep. 25, 2012.

International Search Report and Written Opinion for PCT/US2012/044920, dated Sep. 25, 2012; ISA/US.

"European Application Serial No. 12804228.0, Decision to Grant dated Jul. 14, 2016", 2 pgs.

"European Application Serial No. 12804228.0, Intention to grant dated Feb. 16, 2016", 36 pgs.

"European Application Serial No. 12804228.0, Response filed Apr. 27, 2015 to Extended European Search Report dated Oct. 22, 2014", 21 pgs.

"European Application Serial No. 16183466.8, Extended European Search Report dated Jul. 7, 2017", 8 pgs.

"European Application Serial No. 16183466.8, Response filed Feb. 16, 2018 to Extended European Search Report dated Jul. 7, 2017", 34 pgs.

* cited by examiner

LOCKING MECHANISM TO SECURE ENDS OF AN IMPLANTABLE BAND

CROSS-REFERENCES TO RELATED APPLICATIONS

This application is a 371 U.S. National Stage of International Application No. PCT/US2012/044920, filed Jun. 29, 2012, which claims the benefit of U.S. Provisional Application No. 61/502,615, filed Jun. 29, 2011. The disclosures of the above applications are incorporated herein by reference.

FIELD

The present disclosure relates generally to bone fixation and more particularly to an apparatus and method for joining cut bone portions by securing ends of an implantable fabric that at least partially encircles the bone portions.

BACKGROUND

This section provides background information related to the present disclosure which is not necessarily prior art.

Surgeries are often performed on humans and animals alike to treat a disease or injury. Treatment of a disease or injury often results in the surgeon having to repair a separated bone. In the case of an injury such as a trauma, the surgeon is often required to immobilize the bone portions at the location of the injury to allow the bone to heal over time. In the case of treatment of a disease such as heart disease, the surgeon is often required to cut a patient's sternum to gain access to and perform a procedure on the patient's heart. Once the heart procedure is complete, the cut sternum is repaired by joining the separate ends of the sternum at the surgical location. As with treatment of an injury, the surgeon immobilizes the area of the sternum to allow the sternum to heal over time. Regardless of whether the surgeon is treating an injury or repairing a separated bone necessitated by another surgical procedure, immobilization of the site, as well as application of a compressive force to the bone, hastens the patient's recovery time and affords the bone time to heal.

SUMMARY

This section provides a general summary of the disclosure, and is not a comprehensive disclosure of its full scope or all of its features.

In one aspect, the present disclosure provides a locking mechanism for securing ends of an implantable fabric including a plate member having aperture formed therethrough. A cam member is rotatable relative to the aperture between a locked state and an unlocked state. The implantable fabric is movable relative to the plate member when the cam member is in the unlocked state and restricted from moving relative to the plate member when the cam member is in the locked state.

In another aspect, the present disclosure provides a locking mechanism for an implantable fabric including a plate member. An aperture is formed through the plate member. A pair of retaining fingers extends into the aperture and respectively define a gap between an end of each retaining finger and the plate member. The gaps each have a width that is smaller than a thickness of the implantable fabric and receive the implantable fabric therein. A cam member is rotatably received within the aperture. The cam member is movable between an unlocked state permitting movement of the implantable fabric relative to the plate member with the gaps and a locked state restricting movement of the implantable fabric relative to the plate member.

In still another aspect, the present disclosure provides a method for compressing a bone to promote healing. The method includes passing an implantable fabric through a first opening of a locking plate. Next, the implantable fabric is extended around the bone. The implantable fabric is then passed through a second opening of the locking plate. The implantable fabric is then moved in a first direction within each of the first opening and the second opening to place the implantable fabric under tension. Movement of the implantable fabric is prevented in a second direction, opposite to the first direction, at each of the first opening and the second opening. The implantable fabric is further moved in the first direction. Movement of the implantable fabric is again prevented in the second direction at each of the first opening and the second opening. Finally, a cam member is rotated from an unlocked state to a locked state to fix a position of the implantable fabric relative to the locking plate.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
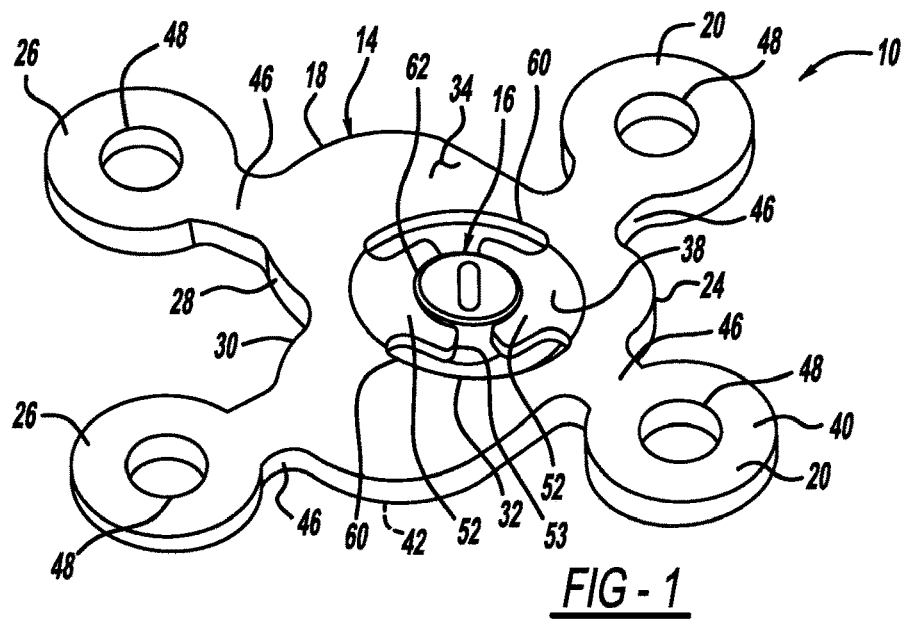
FIG. 1 is a perspective view of a locking mechanism in accordance with the teachings of the present disclosure and in an unlocked state.

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-24, various methods and apparatuses are disclosed according to the present teachings for securing ends of an implantable fabric in a sternal closure operation. However, the various apparatuses and methods may also be used in connection with various other fixation methods and/or procedures. Therefore, it will be understood that the following discussions are not intended to limit the scope of the present teachings or claims herein.

Referring now to FIGS. 1-4 of the drawings, a locking mechanism 10 is shown to include an implantable fabric 12, a locking plate 14 and a center cam 16. Locking mechanism 10 may be used to secure the implantable fabric 12 around a broken, sectioned (cut), or otherwise compromised portion of bone to assist in repairing the bone. Unless specifically mentioned, the various components of the locking mechanism 10 can be made of any suitable biocompatible material including, but not limited to, non-resorbable polymers (e.g., polyethylene or polyester), thermoplastic elastomers, ceramics, and metals (e.g., stainless steel, titanium), or various combinations of these materials. In various aspects, the implantable fabric 12 may be any of various biocompatible monofilament and braided materials of both resorbable and non-resorbable designation. As a non-limiting example, the implantable fabric 12 may be a polymeric fiber, such as a polyethylene, polyester, polyamide, or various combinations thereof. Implantable fabric 12 could also be constructed in any form such as, for example, a weave, a braid, or a knit.

Locking mechanism 10 and/or implantable fabric 12 may also be provided with an antibiotic and/or platelet concentrate coating to resist bacterial adhesion and/or promote healing. In this regard, locking mechanism 10 and fabric 12, as well as other constructs discussed herein, may be pre-configured with such a coating or the coating may be applied intraoperatively. Further, the surgeon may also apply the platelet coating to the sectioned area during the sternal closure procedure.

The locking plate 14 may include a base 18, a first pair of extension portions 20 positioned proximate a first end 24 thereof, a second pair of extension portions 26 positioned proximate a second end 30 thereof, an outer periphery 28 extending between the first and second ends 24, 30, and a contoured aperture 32 centrally located within the base 18. The base 18 and extension portions 20, 26 may further define a common upper surface 34 having a substantially hemispherical shape extending from a substantially flat, central high portion 38 generally arranged at the contoured aperture 32 to a peripheral low point 40 generally arranged at the first and second ends 24, 30. Notably, the central high portion 38 extends about the area defined by the contoured aperture 32. A first, bone-facing lower surface 42 may extend over the base 18 and may be substantially flat over its length to provide the base 18 with a thickness of approximately 0.063-0.043 in from the contoured aperture 32 to the first and second ends 24, 30.

Furthermore, the extension portions 20, 26 may further define a second, substantially flat lower surface 44 at a distance (e.g., 0.020-0.030 in) from the first lower surface 42. The distance between the lower surface 42 and the lower surface 44 provides clearance for the implantable fabric 12 to pass without compression, as will be described in more detail below.

The extension portions 20, 26 may be connected to the base 18 by a plurality of narrowed sections 46. The narrowed sections 46 may be contiguous with both the hemispherical upper surface 34 and the first lower surface 42 to provide a raised, narrow, and thinned region for easy cutting during plate removal. The extension portions 20, 26 may also each include a central aperture 48 for receipt of a fixation member 50 (FIG. 8), such as a self-tapping screw, a spike, a post, an adhesive or the like. While central apertures 48 are shown to be concentrically arranged within rounded extension portions 20, 26, the extension portions 20, 26, may have any appropriately shaped internal and/or external profile (e.g., ovular, rectangular, or other polygonal shape).

As previously described, the contoured aperture 32 may be centrally located within the base 18 and may extend from the central high portion 38 of the common upper surface 34 to the first lower surface 42. The contoured aperture 32 may further define a pair of opposed retaining fingers 52, a pair of hard stops 56, and a pair of opposed cinch openings 60. The opposed retaining fingers 52 may extend inwardly to define a central opening 62 therebetween for receipt of the center cam 16, and may extend from the common upper surface 34 by a distance (e.g., 0.020 in) to define an undersurface 64. The undersurface 64 may incorporate a chamfered edge 66 at the central opening 62.

Furthermore, the hard stops 56 may extend from the undersurface 64 of the opposed retaining fingers 52 to the first lower surface 42 and may be shaped correspondingly to the profile of the center cam 16. In this way, when the center cam 16 is rotatably received within the central opening 62, the hard stops 56 prevent rotation beyond a predetermined angle. The hard stops 56 may have a width that terminates completely within the space defined by the undersurface 64 or may extend to within the space defined by the opposed cinch openings 60.

Figure 2:
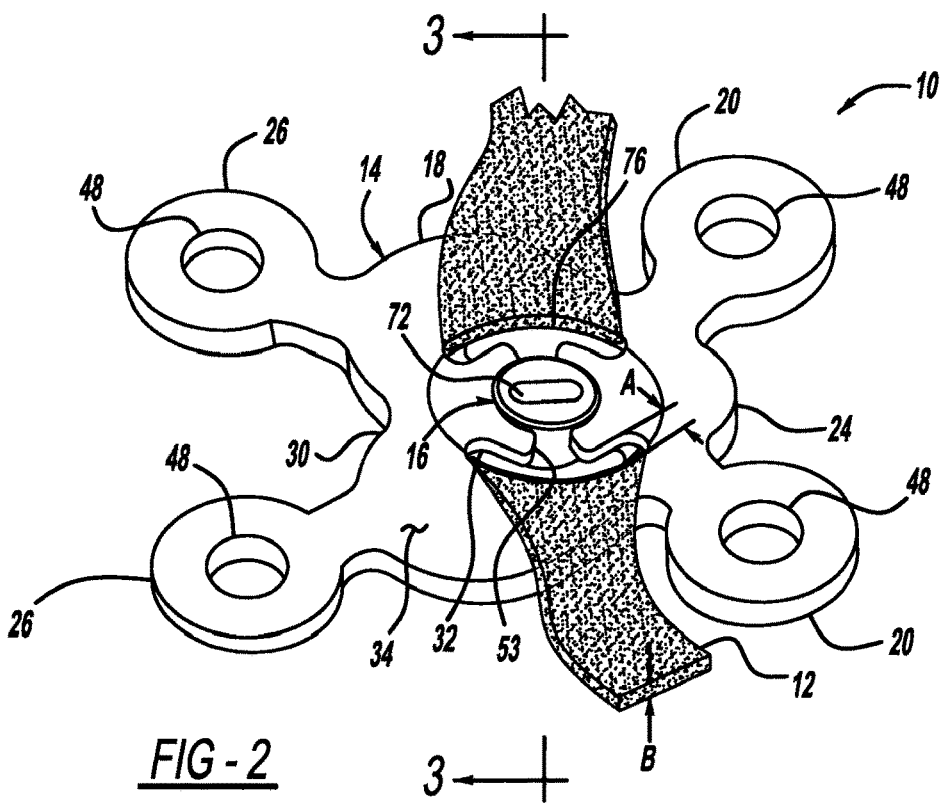
FIG. 2 is a perspective view of the locking mechanism of FIG. 1 in a locked state and incorporating an implantable fabric in accordance with the teachings of the present disclosure.

The opposed cinch openings 60 may be arcuate apertures extending from the common upper surface 34 to the first lower surface 42. The opposed cinch openings 60 may be arranged approximately ninety degrees (90°) from the opposed retaining fingers 52 within the contoured aperture 32. The opposed cinch openings 60 may have a gap width (A) that is less than a thickness (B) of the implantable fabric 12, as best shown in FIG. 2 (e.g., gap width (A) is approximately ⅕ of the size of thickness (B)).

During operation, the implantable fabric 12 is compressed within the cinch openings 60 and is relaxed outside of the cinch openings 60 due to the gap width (A) being less than the braid thickness (B). Furthermore, the extending shape of the retaining fingers 52 may provide a corner 53 that contacts the implantable fabric 12 in an area of the fabric 12 between the compressed and relaxed portions for retaining the woven structure of the implantable fabric 12. As described, the cinch openings 60 and the corner 53 of the retaining fingers 52 cooperate to provide a temporary retention mechanism for the implantable fabric 12 during surgical procedures. For example, when the implantable fabric 12 is drawn through the cinch openings 60 in a direction (X) shown in FIG. 3, the cinch openings 60 and corner 53 cooperate to engage the fabric 12 to restrict the fabric 12 from moving in an opposite direction (Y).

With continued reference to FIGS. 1 through 4, the center cam 16 may define a bow-tie shaped body portion 68, a raised hub 70 centrally located within the body portion 68, and a channel 72 extending at least partially through both the body portion 68 and the raised hub 70. The bow-tie shape of the body portion 68 may include flat locating surfaces 74 for contact with the hard stops 56 and an outer periphery 76 that retains the implantable fabric 12, as will be described in more detail below. Once the center cam 16 is inserted into the locking plate 14 and is rotated from an unlocked state (FIG. 1) to a locked state (FIG. 2), the outer periphery 76 of the body portion 68 may define a gap width (C) between the outer periphery 76 and the contoured aperture 32. The gap width (C) may be smaller than the gap width (A). As such, the implantable fabric 12 may be fixedly retained within the opposed cinch openings 60 at the gap (C) by the outer periphery 76 of the center cam 16 when the center cam 16 is in the locked state.

The body portion 68 may further define an upper surface 78 and a parallel lower surface 80, which provide a thickness to the body portion 68 corresponding to the dimension between the undersurface 64 and the first lower surface 42. In this way, when the center cam 16 is inserted into the locking plate 14, the first lower surface 42 and the lower surface 80 will be coplanar.

As previously disclosed, the raised hub 70 may be centrally located within the body portion 68 and may extend from upper surface 78 by a distance (e.g., 0.032 in), so as to extend above the central high portion 38 after insertion into the locking plate 14. The raised hub 70 may further define a rim 82 extending outwardly from an outer profile 84. The rim 82 may have a chamfered edge 86 along a top surface 88 of the raised hub 70. Furthermore, the channel 72 may also have a chamfered edge 90 along the top surface 88 of the raised hub 70. While the locking mechanism 10 is shown to have four extension portions 20, 26, any number of extension portions are contemplated for use with the locking mechanism 10.

Figure 5:
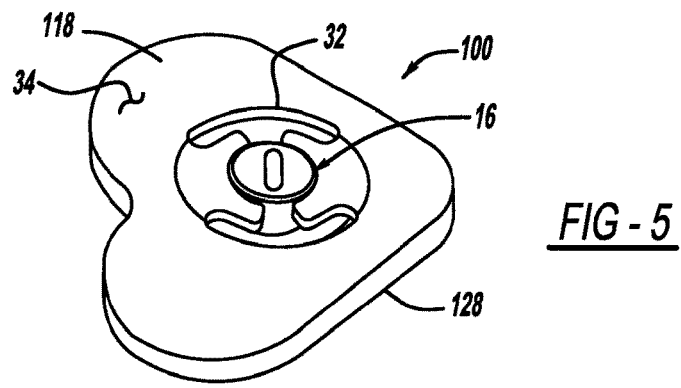
FIG. 5 is a perspective view of a locking mechanism in accordance with the teachings of the present disclosure and in an unlocked state.

With particular reference to FIG. 5, a locking mechanism 100 is provided without extension portions. The locking mechanism 100 is virtually identical to the locking mechanism 10, as the locking mechanism 100 similarly includes the center cam 16, contoured aperture 32, and hemispherical upper surface 34. Because the cam 16, contoured aperture 32, and hemispherical upper surface 34 are identical to those of the locking mechanism 10, a detailed description of the cam 16, contoured aperture 32, and hemispherical upper surface 34 is foregone.

The locking mechanism 100, however, may include a different base 118 when compared to the locking plate 14 of the locking mechanism 10. For example, the base 118 omits extension portions 20, 26 and therefore does not exhibit the stepped lower surface 42, 44 of the locking mechanism 10. As such, the locking mechanism 100 has a smaller size, but does not provide a dedicated clearance zone for the implantable fabric 12 to pass. When used in certain locations of the body, however, the stepped portion may be unnecessary as the fabric 12 passes freely due to bone shape and surface roughness. In this configuration, the base 118 may still include the hemispherical upper surface 34 to provide a comfortable fit when utilized in repairing a sternum (FIGS. 8-11).

Figure 6:
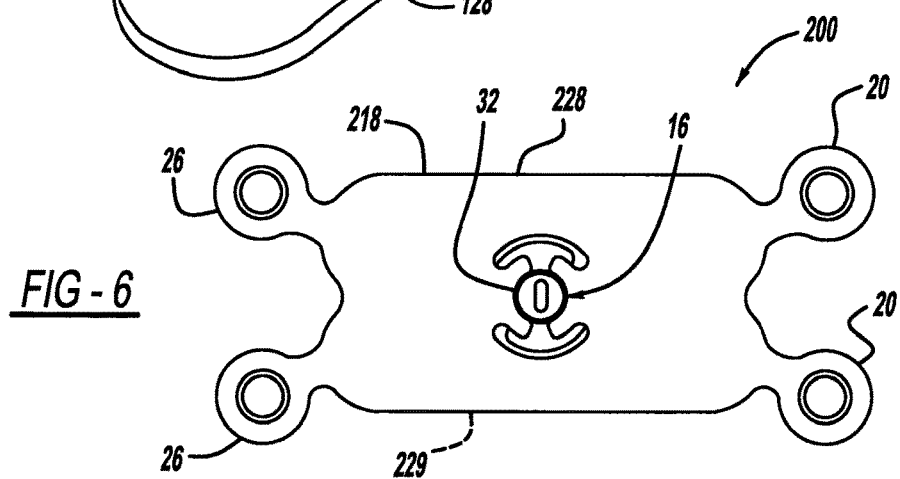
FIG. 6 is a top view of a locking mechanism in accordance with the teachings of the present disclosure and in an unlocked state.
Figure 7:
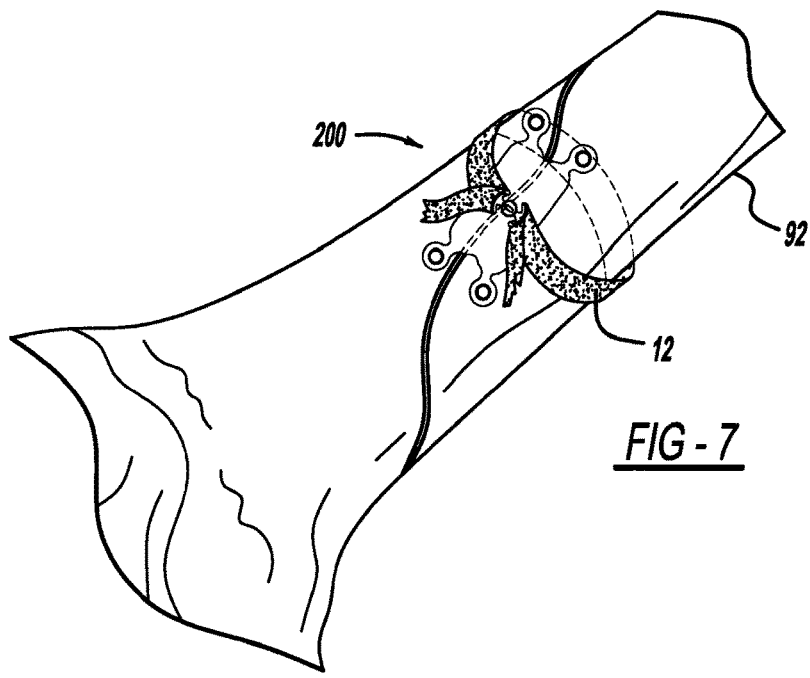
FIG. 7 is a perspective view of the locking mechanism of FIG. 6 operatively associated with a bone.

Furthermore, while the base 18 of the locking mechanism 10 is shown as having a substantially heart-shaped outer periphery 28, the outer periphery could include virtually any shape. For example, the shape of the base 18 may be polygonal. As shown in FIGS. 6 and 7, an alternative locking mechanism 200 is provided and may include a substantially rectangular base 218 having an outer periphery 228. The rectangular shape of the base 218 is beneficial when used for repairing a long bone 92 (FIG. 7), as the base 218 spans a length of the bone 92. Further, the base 218 may include a contour on a lower surface 229 thereof that is shaped to mimic the curvature of the bone 92. As with the locking mechanism 10, the locking mechanism 200 similarly includes the center cam 16, contoured aperture 32, and extension portions 20, 26. Because the cam 16, contoured aperture 32, and extension portions 20, 26 are identical to those of the locking mechanism 10, a detailed description of the cam 16, contoured aperture 32, and extension portions 20, 26 is foregone.

Figure 3:
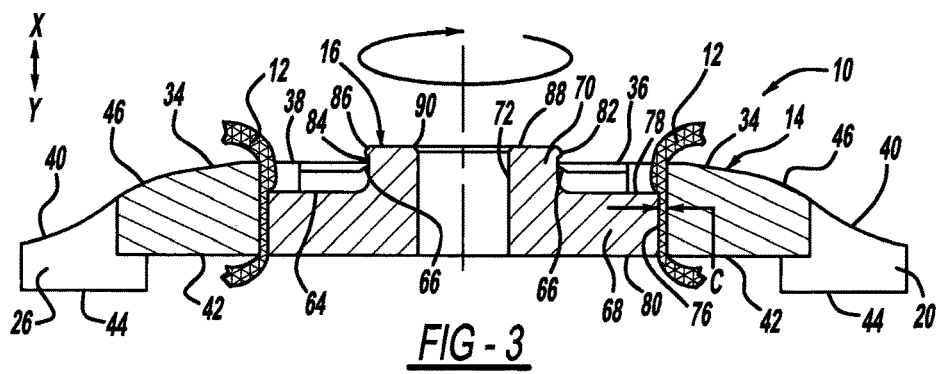
FIG. 3 is a sectional view of the locking mechanism of FIG. 2 taken along line 3-3 of FIG. 2.
Figure 4:
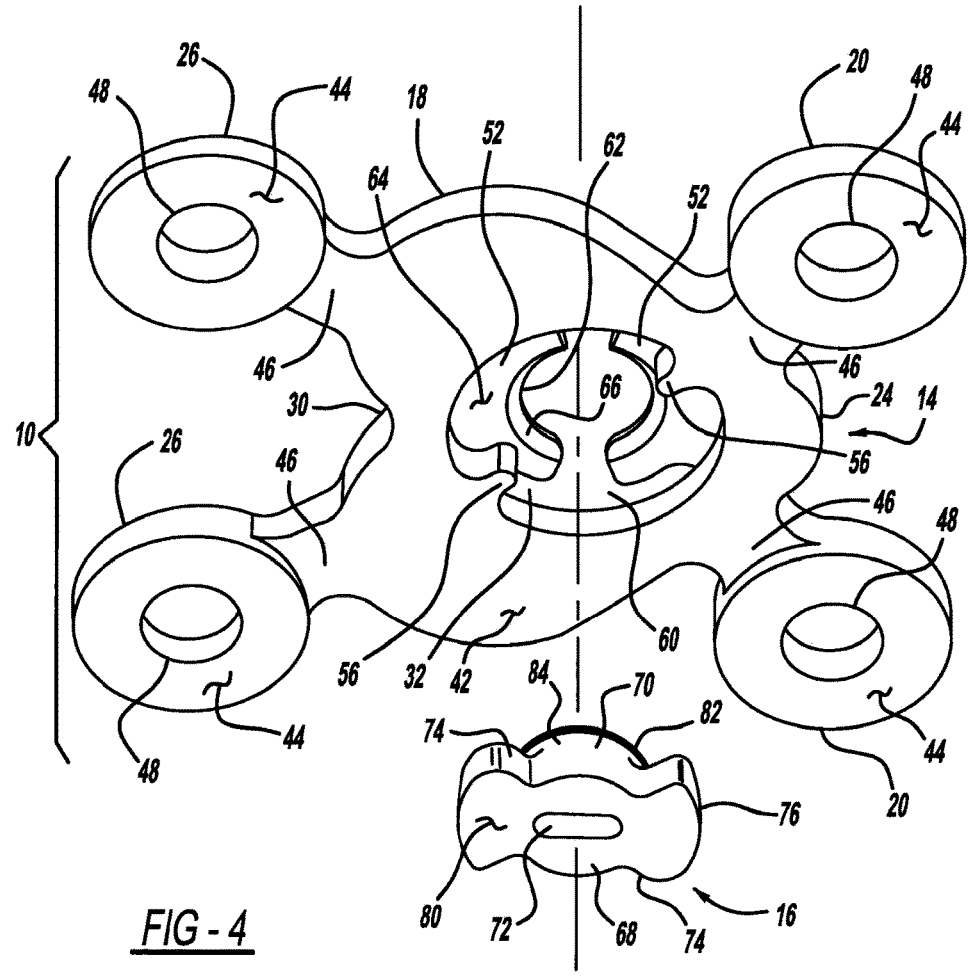
FIG. 4 is an exploded view of the locking mechanism of FIG. 1.

Operation of the locking mechanism 10 will now be described in greater detail with reference to an exemplary configuration where locking mechanism 10 is wrapped around or compressively encircles a sternum 94, as shown in FIGS. 8-11. The locking mechanism 10 may be pre-assembled prior to delivery to the surgical site. For example, pre-assembly of the locking mechanism 10 may include snap-fitting the center cam 16 into the locking plate 14, as best shown in FIG. 3. In so doing, the rim 82 may be introduced to the undersurface 64 of the opposed retaining fingers 52 by bringing the chamfered edge 86 into contact with the chamfered edge 66. As the chamfered edge 66 is somewhat wider than the central opening 62, the rim 82 must deflect slightly inwardly to allow the raised hub 70 to extend through the central opening 62. After full insertion, the lower surfaces 42, 44 are substantially coplanar. Furthermore, the rim 82 prevents the center cam 16 from backing out of the locking plate 14. The center cam 16 may then be rotated to place the outer periphery 76 within the quadrant defined by the opposed retaining fingers 52.

Figure 8:
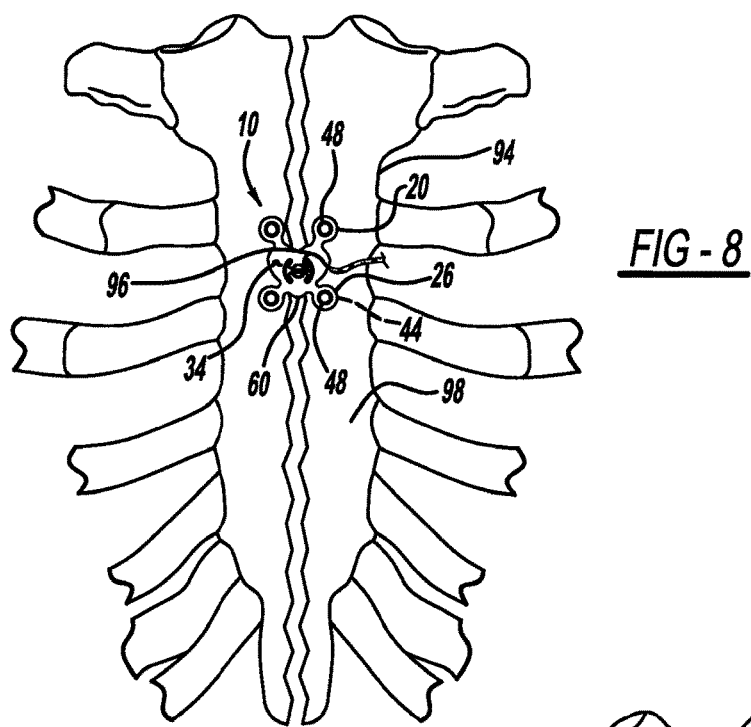
FIG. 8 is a partial perspective view of a cut sternum incorporating a locking mechanism in accordance with the teachings of the present disclosure.

In some configurations, the locking mechanism 10 may be provided with the implantable fabric 12 extending through one of the opposed cinch openings 60, as shown in FIG. 8. Alternately, the implantable fabric 12 may be introduced to the locking mechanism 10 at the surgical site. In either case, the implantable fabric 12 may extend from a curved needle 96 for ease in threading through the surgical site and the locking mechanism 10.

Accordingly and with reference to FIG. 8, the pre-assembled locking mechanism 10 may be placed with the lower surface 44 positioned against an anterior side 98 of the sternum 94. The implantable fabric 12 may then be wrapped around the sternum 94 through one of the intercostal spaces. The implantable fabric 12 may then be re-introduced to the locking mechanism 10 by extending the curved needle 96 through the other of the opposed cinch openings 60, from the lower surface 44 towards the upper surface 34.

Figure 9:
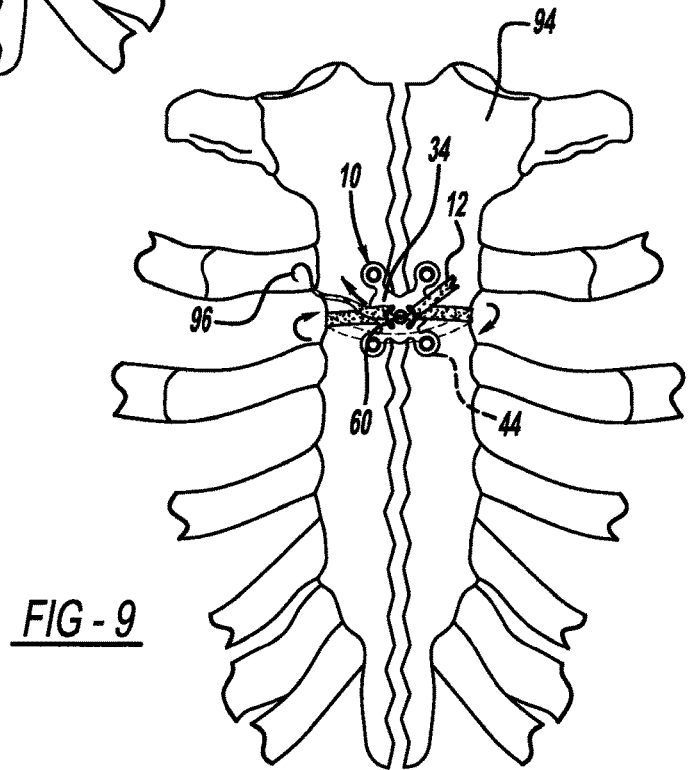
FIG. 9 is a partial perspective view of the sternum and locking mechanism of FIG. 8 in accordance with the teachings of the present disclosure having a fabric extending partially around the cut sternum and extending through the locking mechanism.

With reference now to FIG. 9, the implantable fabric 12 may then be hand-tightened to bring the sternum 94 into alignment by applying a force to the fabric 12 in a direction substantially away from the sternum 94. As previously discussed, when the implantable fabric 12 extends into the opposed cinch openings 60, the gap width (A) of the cinch openings 60 is less than the relaxed braid thickness (B). Accordingly, the locking mechanism 10 does not require an additional tool for initially reducing the sternum 94. Furthermore, the distance between the lower surface 42 and the lower surface 44 provides freedom for the implantable fabric 12 to move without being compressed between the locking mechanism 10 and the sternum 94.

Figure 10:
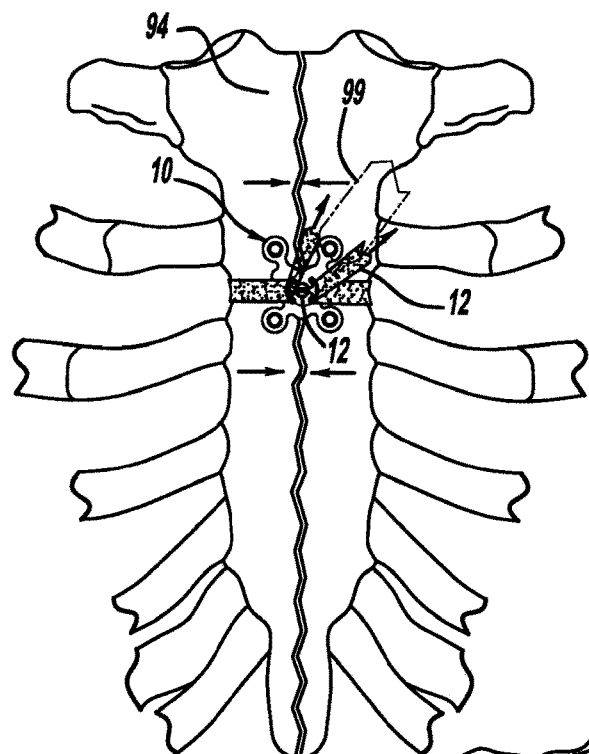
FIG. 10 is a partial perspective view of the sternum and locking mechanism of FIG. 9 illustrating an additional tensioning force being applied to the fabric via a tool to draw the sternum together.

Referring now to FIG. 10, after the sternum 94 is reduced as much as possible by hand tightening, a tool 99 is introduced to the locking mechanism 10 to further tighten the implantable fabric 12 and to bring the separated portions of the sternum 94 in close proximity with one. The tool 99 may be shaped so as to extend into the channel 72 for retention therewith. The implantable fabric 12 may be secured to the tool 99 and may be further tightened, so as to bring the sternum 94 into a final compressed position.

Figure 11:
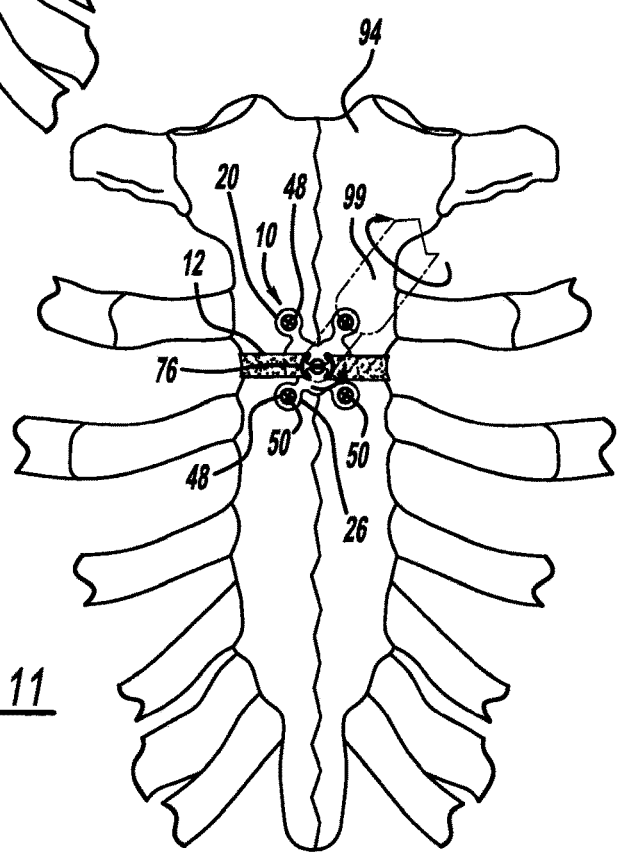
FIG. 11 is a partial perspective view of the sternum and locking mechanism of FIG. 8 illustrating the locking mechanism in a locked state and fixedly attached to both sides of the cut sternum.

With reference now to FIG. 11, the tool 99 may then be rotated to lock the outer periphery 76 of the center cam 16 against the implantable fabric 12. Optionally, the locking mechanism 10 may then be fixedly secured across the sternum 94 by extending fixation members 50 through the central apertures 48 of each of the extension portions 20, 26. After the locking mechanism 10 is moved to the final locked position as shown in FIG. 11, the implantable fabric 12 may then be trimmed. Any device for trimming the implantable fabric 12 is contemplated, such as, for example, scissors or a scalpel. Additionally, a cauterizing tool (not shown) may be used to remove the excess fabric 12. While removing the excess fabric 12, heat from the cauterizing tool can melt the ends of the individual fibers together, reducing the likelihood of fraying and reducing fabric flexibility. Furthermore, the cauterized fabric is enlarged or mushroomed over the center cam 16, further increasing the thickness (B) for preventing fabric pullout.

Figure 12:
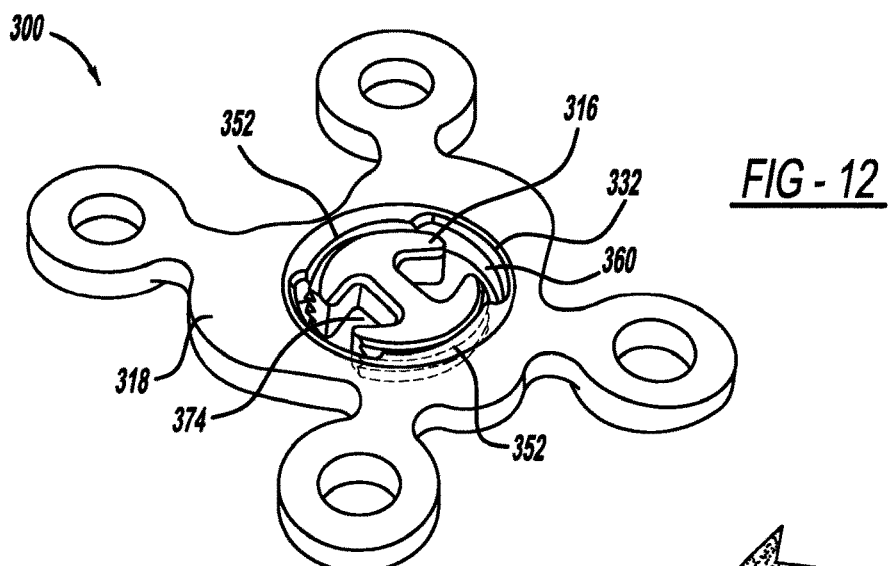
FIG. 12 is a perspective view of a locking mechanism in accordance with the teachings of the present disclosure and in an unlocked state.
Figure 13:
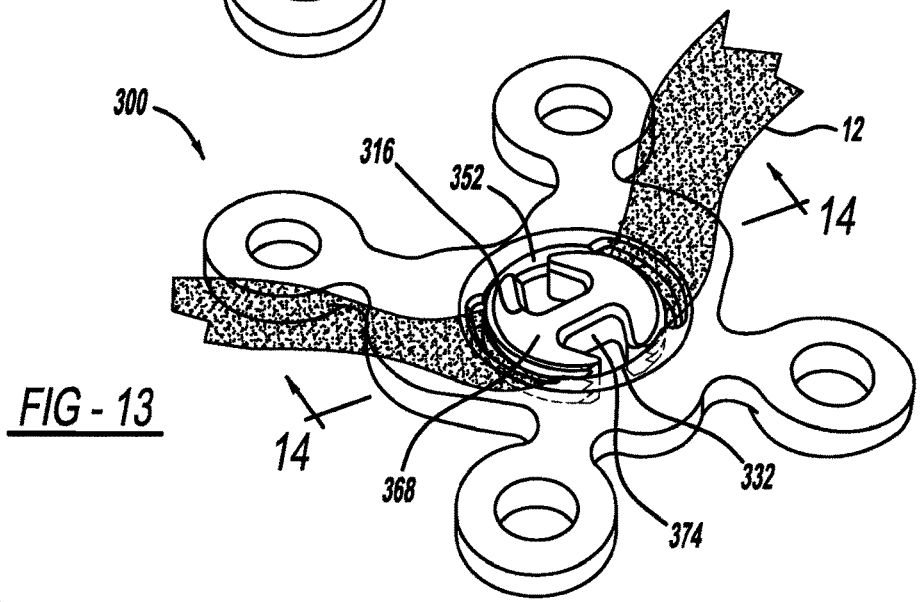
FIG. 13 is a perspective view of the locking mechanism of FIG. 12 in a locked state and incorporating an implantable fabric in accordance with the teachings of the present disclosure.
Figure 14:
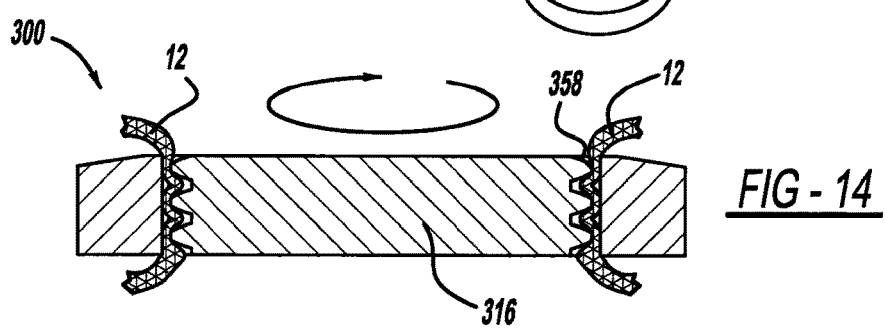
FIG. 14 is a sectional view of the locking mechanism of FIG. 13 taken along line 14-14 of FIG. 13.

With particular reference to FIGS. 12-14, a locking mechanism 300 is provided. Locking mechanism 300 may be used to secure an implantable fabric 12 around a bone to assist in repairing the bone, as previously described with respect to locking mechanisms 10, 100, and 200. The locking mechanism may include a center cam 316 and a contoured aperture 332 associated with a base 318. The contoured aperture 332 may be centrally located within the base 318 and may include a pair of internal threaded surfaces 352. The internal threaded surfaces 352 may matingly correspond to a tooth profile 358 of the center cam 316 to allow the center cam 316 to be threadably received by the contoured aperture 332. The center cam 316 may include a body portion 368 having generally trapezoidal cutouts 374. The trapezoidal cutouts 374 of the body portion 368 provide the center cam 316 with a reduced-weight design and also with a receiving location for the curved needle 96.

The locking mechanism 300 operates in a similar fashion as the locking mechanism 10. For example, the locking mechanism 300 may be pre-assembled by threading the center cam 316 into the contoured aperture 332 prior to delivery of the locking mechanism 300 to the surgical site. The center cam 316 may be threaded into the contoured aperture 332 until the tooth profile 358 is within the quadrant defined by the internal threaded surfaces 352 and the trapezoidal cutouts 374 are aligned with opposed cinch openings 360 (FIG. 12). The implantable fabric 12 may then be threaded into the locking mechanism 300 before or after being placed in the surgical site, as previously described. In particular, the curved needle 96 may be passed through one of the trapezoidal cutouts 374, around the bone, and back through the other of the trapezoidal cutouts 374.

The implantable fabric 12 may be hand-tightened to bring the bone portions into alignment in a similar fashion as described with respect to FIG. 10. After the bone is reduced as much as possible, the tool 99 may be used to further compress the bone and to rotate the tooth profile 358 of the center cam 316 into the cinch openings 360 (FIG. 13). In this way, the tooth profile 358 of the center cam 316 compresses the implantable fabric 12 against the contoured aperture 332 for retention therewith (FIG. 14).

Figure 15:
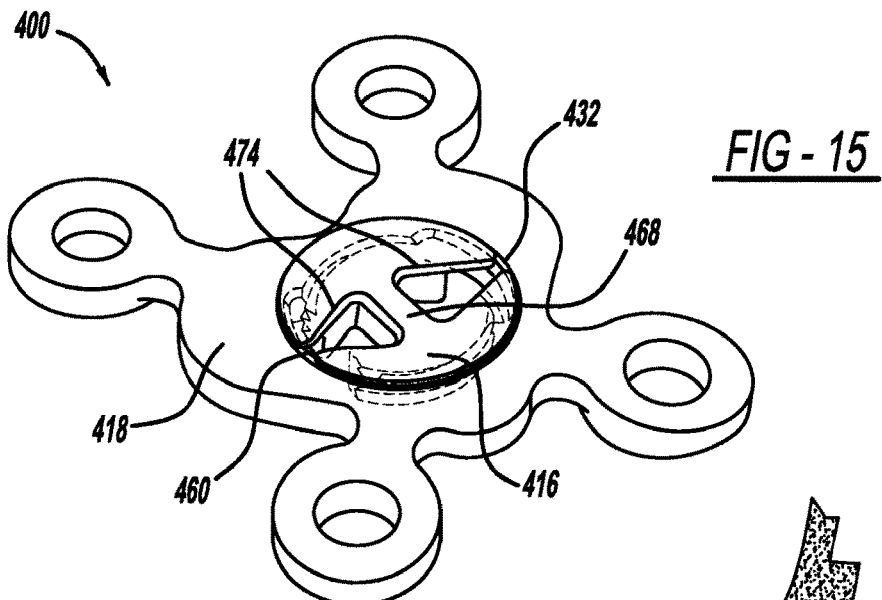
FIG. 15 is a perspective view of a locking mechanism in accordance with the teachings of the present disclosure and in an unlocked state.
Figure 16:
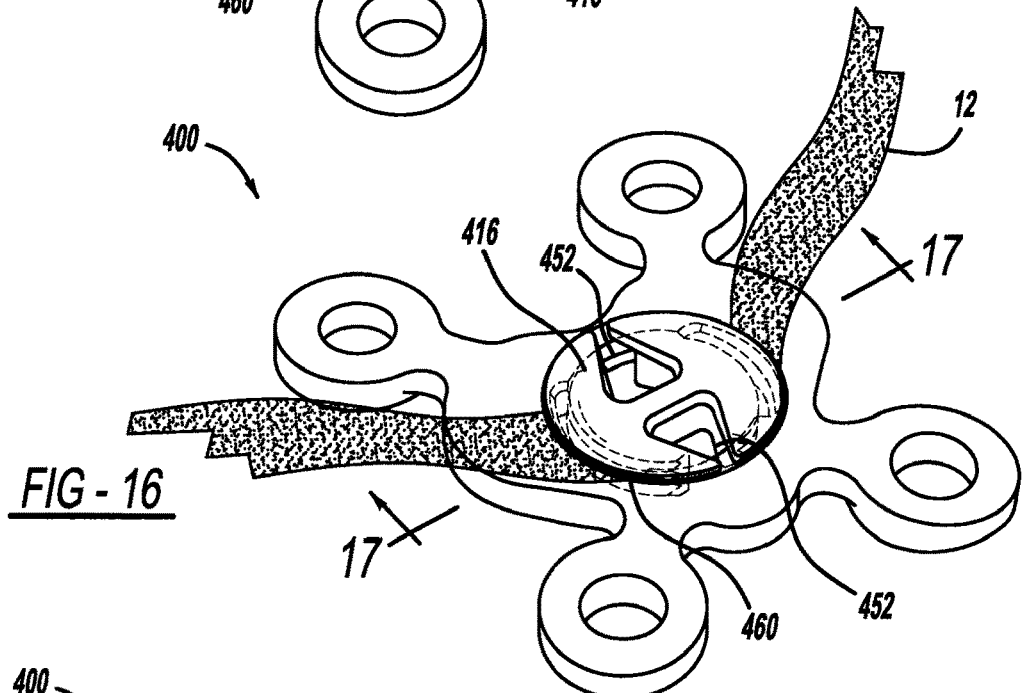
FIG. 16 is a perspective view of the locking mechanism of FIG. 15 in a locked state and incorporating an implantable fabric in accordance with the teachings of the present disclosure.
Figure 17:
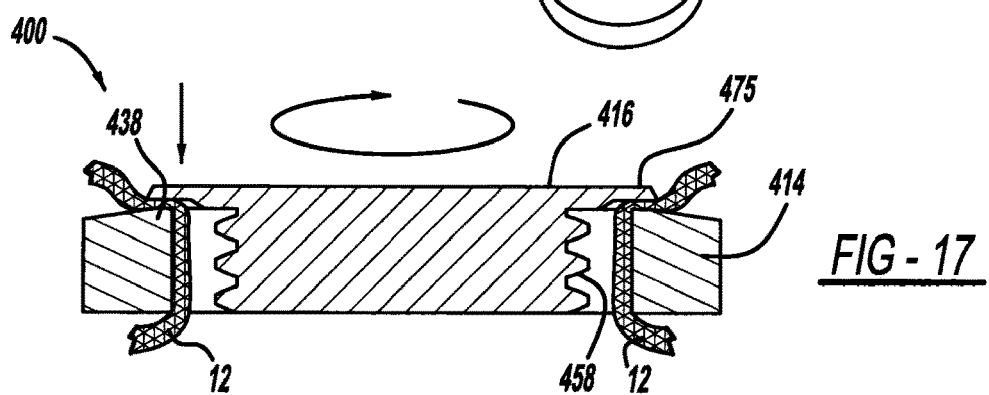
FIG. 17 is a sectional view of the locking mechanism of FIG. 16 taken along line 17-17 of FIG. 16.

With particular reference to FIGS. 15-17, a locking mechanism 400 is provided for securing an implantable fabric 12 around a bone to assist in repairing the bone. The locking mechanism 400 includes a center cam 416, a base 418, and a contoured aperture 432 for retaining the implantable fabric 12. As with the locking mechanism 10, the contoured aperture 432 may be centrally located within the base 418. The contoured aperture 432, however, may define a pair of internal threaded surfaces 452 in place of the opposed retaining fingers 52 of the locking mechanism 10. The internal threaded surfaces 452 may matingly correspond to a tooth profile 458 of the center cam 416 to allow, the center cam 416 to be threadably received by the contoured aperture 432. The center cam 416 may define a body portion 468 having generally trapezoidal cutouts 474 and a flange 475 extending over a central high portion 438 of the locking plate 414. The trapezoidal cutouts 474 of the body portion 468 provide the locking mechanism 400 with a reduced-weight design and a widened receiving location for the curved needle 96.

The locking mechanism 400 operates in a similar fashion as the locking mechanism 10. For example, before delivery to the surgical site, the locking mechanism 400 may be pre-assembled by threading the center cam 416 into the contoured aperture 432. The center cam 416 may be rotated into the contoured aperture 432 until the tooth profile 458 is within the quadrant defined by the internal threaded surfaces 452 and the trapezoidal cutouts 474 are in alignment with the opposed cinch openings 460 (FIG. 15). The implantable fabric 12 may then be threaded into the locking mechanism 400 before or after being placed in the surgical site, as previously described. In particular, the curved needle 96 may be passed through one of the trapezoidal cutouts 474, around the bone, and back through the other of the trapezoidal cutouts 474.

The implantable fabric 12 may be hand-tightened to bring the bone portions into alignment in a similar fashion as described with respect to FIG. 10. After the bone is reduced as much as possible, the tool 99 may be used to further compress the bone portions and to rotate the tooth profile 458 of the center cam 416 into the cinch openings 460 (FIG. 16). As the tooth profile 458 of the center cam 416 may define a substantially smaller diameter than that of the contoured aperture 432, the implantable fabric 12 may be retained by being compressed between the flange 475 and the central high portion 438 of the locking plate 414 (FIG. 17).

Figure 18:
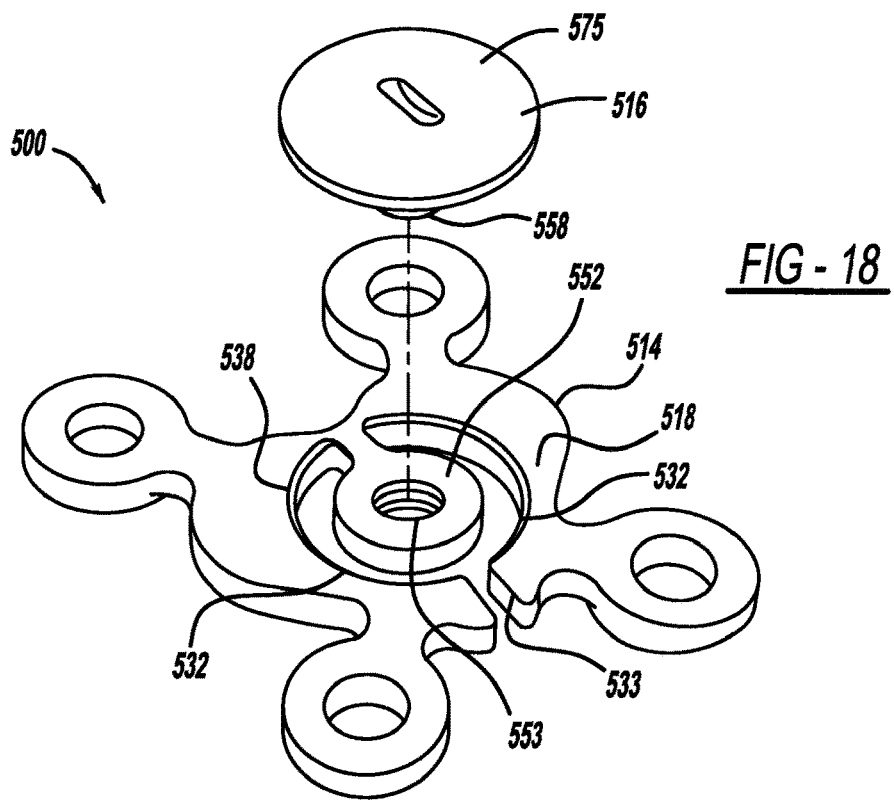
FIG. 18 is an exploded view of a locking mechanism in accordance with the teachings of the present disclosure and in an unlocked state.
Figure 19:
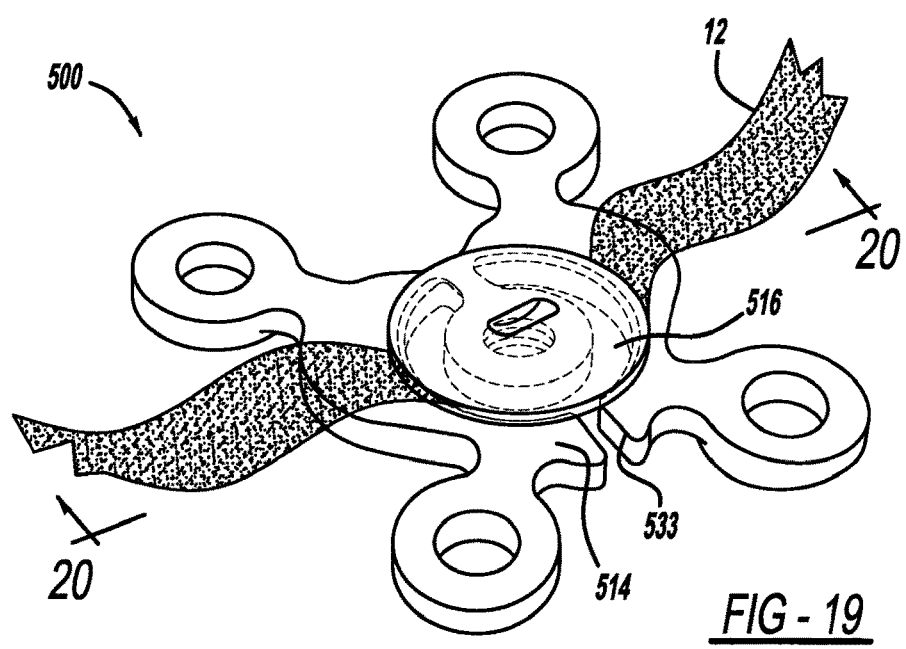
FIG. 19 is a perspective view of the locking mechanism of FIG. 18 in a locked state and incorporating an implantable fabric in accordance with the teachings of the present disclosure.
Figure 20:
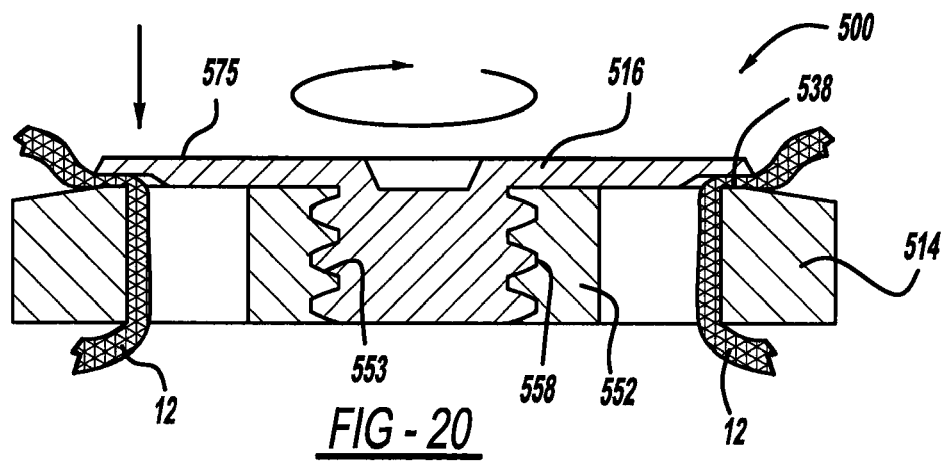
FIG. 20 is a sectional view of the locking mechanism of FIG. 19 taken along line 20-20 of FIG. 19.

With particular reference to FIGS. 18-20, a locking mechanism 500 is provided for use in securing an implantable fabric 12 around a bone to assist in repairing the bone. The locking mechanism 500 may include a center cam 516, a base 518, and a contoured aperture 532 for retaining the implantable fabric 12. The contoured aperture 532 may be centrally located within the base 518 and may include a peninsular member 552 having a threaded central aperture 553. A slot 533 may extend through the locking plate 514 to the contoured aperture 532. The threaded central aperture 553 may matingly correspond to a tooth profile 558 of the center cam 516 to allow the center cam 516 to be threadably received by the threaded central aperture 553. The center cam 516 may define an enlarged flange portion 575 extending over a central high portion 538 of the locking plate 514.

The locking mechanism 500 operates in a similar fashion as the locking mechanism 10. For example, before delivery to the surgical site, the locking mechanism 500 may be pre-assembled by threading the center cam 516 into the peninsular member 552 within the contoured aperture 532. The implantable fabric 12 may then be threaded into the locking mechanism 500 before or after being placed in the surgical site. In particular, the curved needle 96 may be passed through the slot 533, into the contoured aperture 532, around the bone, and back through the other end of the contoured aperture 532 by way of the slot 533.

The implantable fabric 12 may still be hand-tightened to bring the bone portions into alignment in a similar manner as described with respect to FIG. 10. After the bone is reduced as much as possible, the tool 99 may be used to further compress the bone and to rotate the center cam 516 further into the peninsular member 552. As the peninsular member 552 fully secures the center cam 516, the implantable fabric 12 may be retained by being compressed between the flange 575 and the central high portion 538 of the locking plate 514 (FIG. 20).

Figure 21:
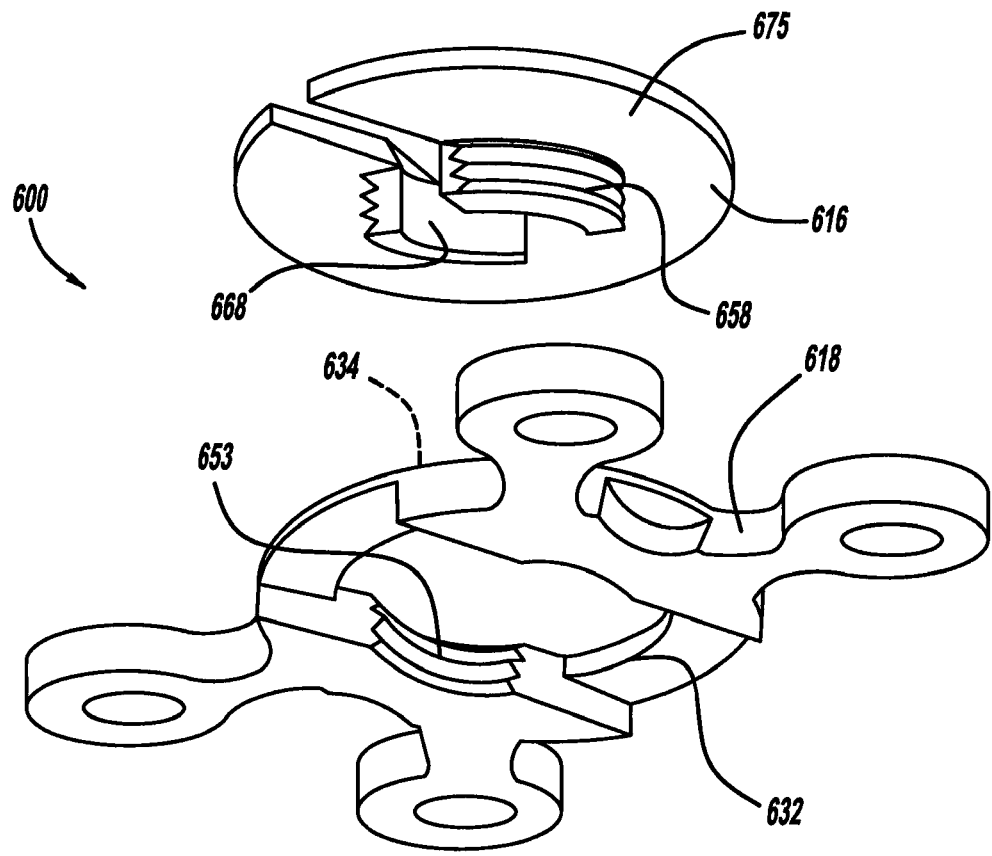
FIG. 21 is an exploded view of a locking mechanism in accordance with the teachings of the present disclosure.
Figure 22:
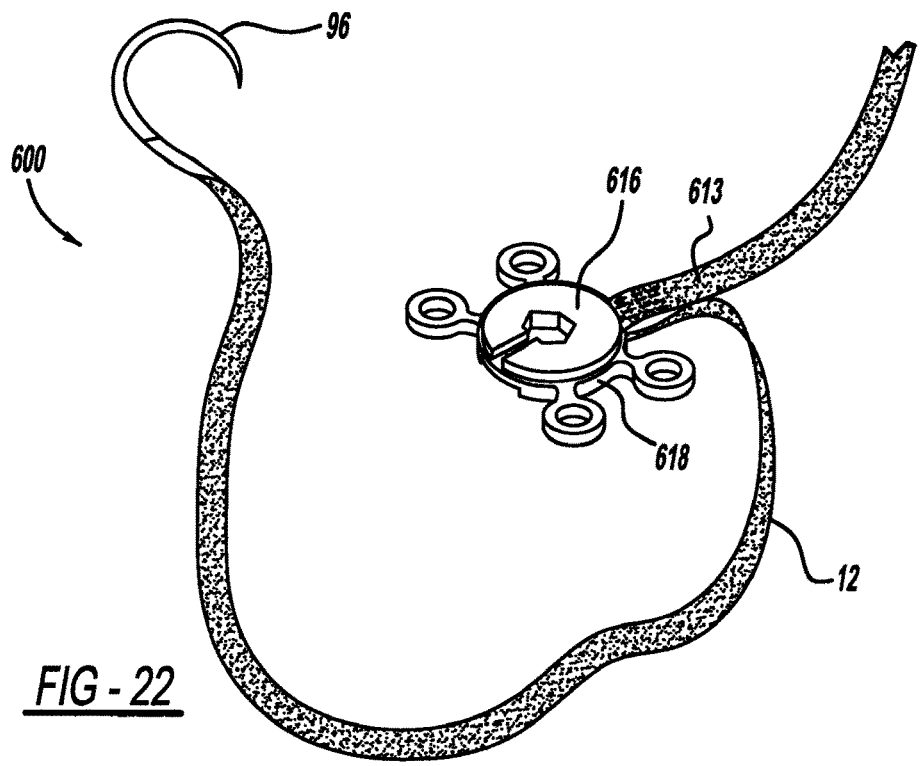
FIG. 22 is a perspective view of the locking mechanism of FIG. 21 incorporating a pre-assembled implantable fabric in accordance with the teachings of the present disclosure.
Figure 23:
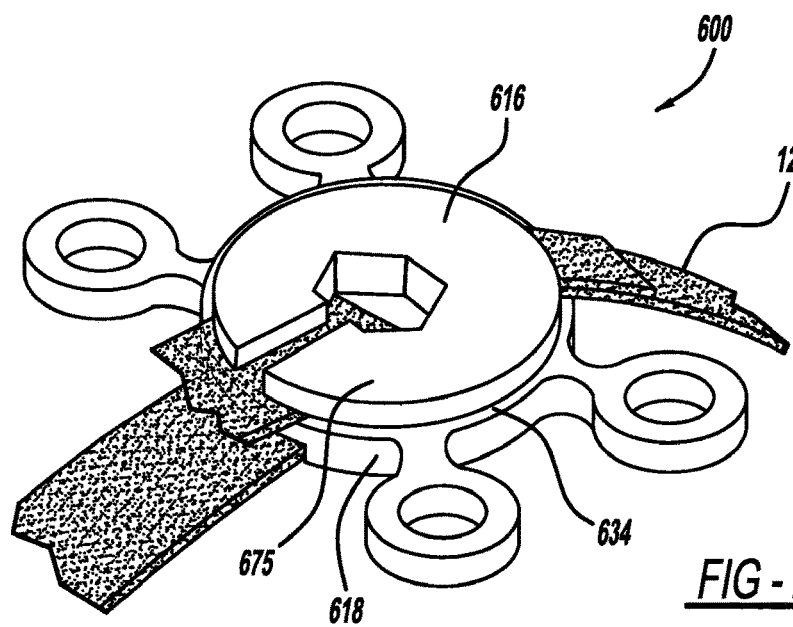
FIG. 23 is a perspective view of the locking mechanism of FIG. 22 in a locked state.

With particular reference to FIGS. 21-23, a locking mechanism 600 is provided for securing an implantable fabric 12 around a bone to assist in repairing the bone. The locking mechanism 600 may include a center cam 616, a base 618, and a contoured aperture 632 for retaining the implantable fabric 12.

As previously described with respect to the locking mechanism 10, the contoured aperture 632 may be centrally located within the base 618. The contoured aperture 632 may define a threaded central aperture 653 that matingly corresponds to a tooth profile 658 of the center cam 616 to allow the center cam 616 to be threadably received by the threaded central aperture 653. The center cam 616 may define an enlarged flange portion 675 extending substantially completely over an upper surface 634 of the base 618.

The locking mechanism 600 operates in a similar fashion as the locking mechanism 10. For example, a first end 613 of the implantable fabric 12 may be secured to the base 618 by stitching before delivery to the surgical site. The locking mechanism 600 may then be pre-assembled by threading the center cam 616 into the contoured aperture 632. After introduction to the surgical site, the implantable fabric 12 may then be attached to the locking mechanism 600 before or after being placed in the surgical site. In particular, the curved needle 96 may be passed from through the contoured aperture 632, around the bone, and back through the other end of the contoured aperture 632.

The implantable fabric 12 may be hand-tightened to bring the bone portions into alignment in a similar fashion as described with respect to FIG. 10. After the bone is reduced as much as possible, the tool 99 may be used to further compress the bone and to rotate the center cam 616 into the contoured aperture 632. As the contoured aperture 632 fully secures the center cam 616, the implantable fabric 12 may be retained by being compressed between the flange 675 and the upper surface 634 of the locking plate 614 (FIG. 23).

Figure 24:
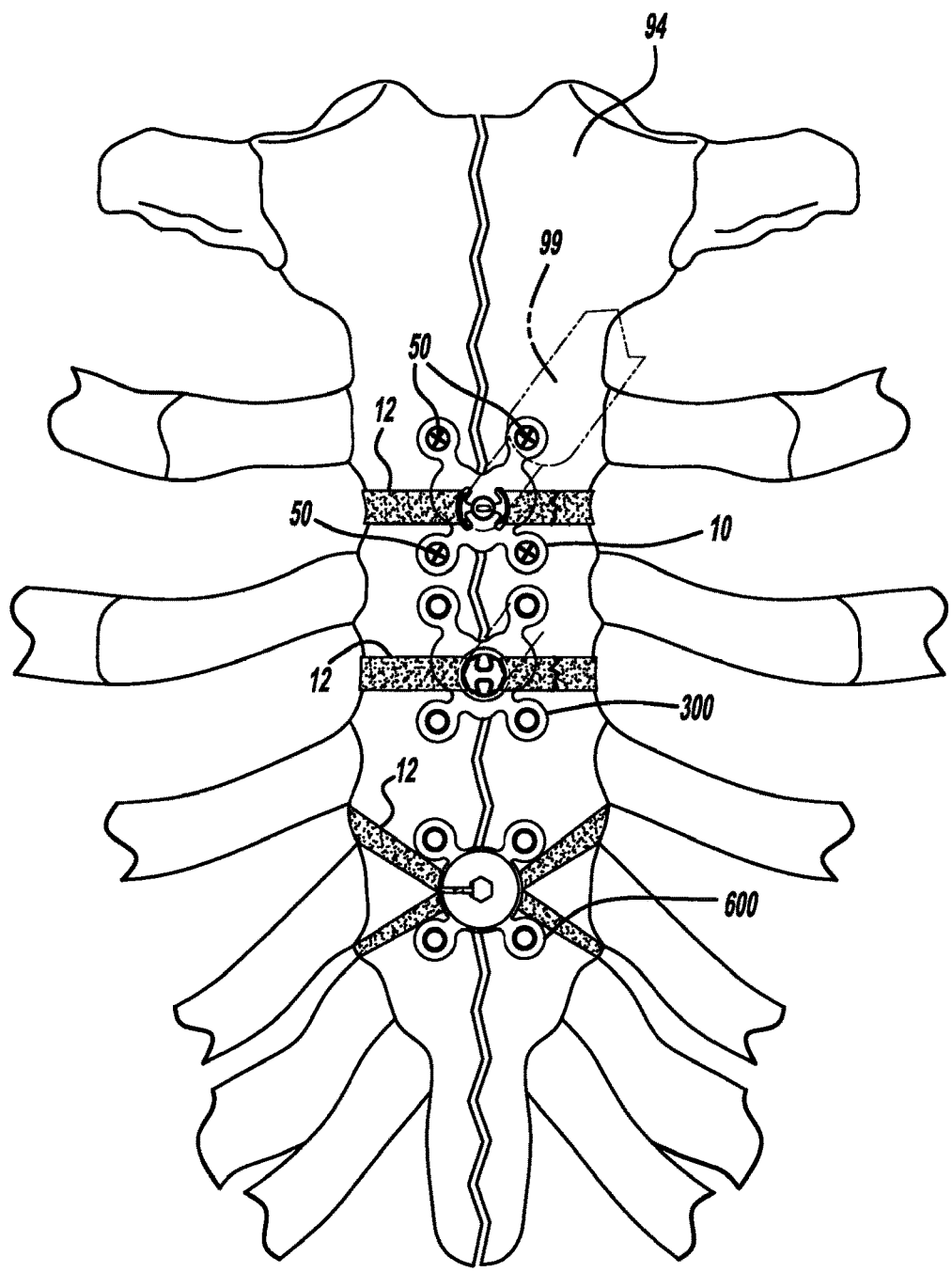
FIG. 24 is a perspective view of the locking mechanisms of FIGS. 2, 13, and 23 associated with a cut sternum.

With particular reference to FIG. 24, several of the locking mechanisms 10, 300, 600 are shown operatively associated with the sternum 94. The locking mechanisms 10, 300, 600 are shown in various configurations for compressing the sternum 94 after a median sternotomy. In particular, the various locking mechanisms 10, 300, 600 may be used in tandem for added compressive support of the sternum 94. Furthermore, the implantable fabric 12 may be crossed in a diagonal pattern for added strength as shown operatively associated with the locking mechanism 600.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A surgically implantable device for securing first and second portions of a surgically implantable band, the device comprising:
   a surgically implantable plate including a first aperture extending therethrough and a retaining member extending radially into the first aperture, the retaining member at least partially defining a second aperture in communication with the first aperture, the first and second portions of the band extending through the first aperture radially outside of the second aperture; and
   a surgically implantable cam member received in the first aperture between the first and second portions and engaging threads of the second aperture for rotation relative thereto between an unlocked state in which at least one of the first and second portions is allowed to move relative to the plate and a locked state in which a clamping force between the plate and the cam member restricts movement of the at least one of the first and second portions relative to the plate, wherein the plate and the cam define a gap sized to receive the band and rotation of the cam relative to the plate from the unlocked state to the locked state cause a width of the gap to reduce.

2. The surgically implantable device of claim 1, wherein both of the first and second portions are allowed to move relative to the plate in the unlocked state and both of the first and second portions are clamped between the plate and the cam member in the locked state.

3. The surgically implantable device of claim 1, wherein the first and second portions are clamped radially between a radially outermost surface of the cam member and a diametrical surface defining the outer periphery of the first aperture.

4. The surgically implantable device of claim 1, wherein the first and second portions are clamped between a first surface of the plate that is substantially perpendicular to a longitudinal axis of the first aperture and a second surface of the cam member that is substantially parallel to the first surface.

5. The surgically implantable device of claim 1, wherein the retaining member includes a pair of cantilevered fingers extending radially inward toward each other and defining the second aperture therebetween.

6. The surgically implantable device of claim 1, wherein the retaining member includes a single cantilevered member including a stem portion and a loop portion disposed at a radially innermost end of the stem portion, the loop portion defining the second aperture.

7. The surgically implantable device of claim 1, wherein the first and second apertures share a common longitudinal axis.

8. The surgically implantable device of claim 1, wherein the cam member includes a central hub portion and a rim portion extending radially outward from the hub portion, the hub portion engaging the threads of the second aperture, the rim portion directly engaging the band in the locked state.

9. The surgically implantable device of claim 1, wherein the plate includes a body portion and a plurality of legs extending outward therefrom, the first aperture extending through the body portion, each of the plurality of legs including a third aperture extending therethrough and adapted to receive a fastener for securing the plate to bodily tissue.

10. The surgically implantable device of claim 1, wherein the plate includes a hard stop extending radially into to the first aperture and preventing rotation of the cam member in one rotational direction when the cam member is in the locked state.

11. The surgically implantable device of claim 1, wherein the cam member includes a pair of cutouts disposed radially opposite each other and extending radially outward through a radial periphery of the cam member, the cutouts extending through an entire axial thickness of the cam member.

12. The surgically implantable device of claim 11, wherein the cam member includes a pair of threaded peripheral surfaces separated from each other by the cutouts, the threads of the threaded peripheral surfaces directly engaging the first and second portions of the band in the locked state to restrict movement of the first and second portions.

13. The surgically implantable device of claim 1, wherein the band is formed from a flat and elongated woven material.

14. A locking mechanism for securing a surgically implantable band, the locking mechanism comprising:

a surgically implantable plate member having an aperture extending therethrough and a pair of retaining fingers extending into the aperture and each defining a respective gap between an end of each retaining finger and the plate member, the gaps each having a width that is smaller than a thickness of the implantable band and receiving the implantable band therein; and a surgically implantable cam member rotatably received within the aperture and rotatable between an unlocked state and a locked state, wherein rotation from the unlocked state to the locked state reduces a width of the gaps restricting movement of the band relative to the plate member.

15. The locking mechanism of claim 14, wherein the retaining fingers are configured to rotatably receive the cam member.

16. The locking mechanism of claim 15, wherein the cam member includes an outwardly extending rim for securing the cam member within the retaining fingers.

17. The locking mechanism of claim 14, wherein the plate member includes a pair of hard stops proximate to the aperture and operable to prevent rotation of the cam member beyond a predetermined angle.

18. The locking mechanism of claim 14, wherein the aperture is threaded.

19. The locking mechanism of claim 18, wherein the outer profile of the cam member includes a tooth profile matingly received by the aperture.

20. The locking mechanism of claim 19, wherein the cam member includes a plurality of cutouts that receive the band.

21. The locking mechanism of claim 19, wherein the tooth profile engages the band when the cam member is in the locked state.

22. The locking mechanism of claim 14, wherein the cam member includes a flange at an upper surface thereof that engages the band when the cam member is in the locked state.

23. The locking mechanism of claim 14, wherein the gaps receive opposite ends of the band therein.

24. The locking member of claim 14, further comprising a retaining element extending into each of the gaps and operable to engage the band at respective ends thereof, the retaining elements permitting movement of the hand in a first direction when the cam member is in the unlocked state and restricting movement of the band in a second direction, opposite the first direction, when the cam member is in the unlocked state.

25. The locking member of claim 14, wherein the plate includes a body portion and a plurality of legs extending outward therefrom, the aperture extending through the body portion, each of the plurality of legs including a mounting aperture extending therethrough and adapted to receive a fastener for securing the plate to bodily tissue.

26. The surgically implantable device of claim 14, wherein the band is formed from a flat and elongated woven material.

27. The surgically implantable device of claim 1, wherein the cam member is configured to rotate about an axis extending transverse to the plate.

* * * * *

UNITED STATES PATENT AND TRADEMARK OFFICE
CERTIFICATE OF CORRECTION

PATENT NO. : 10,058,364 B2
APPLICATION NO. : 14/128862
DATED : August 28, 2018
INVENTOR(S) : Saddy R. Garcia Page 1 of 1

It is certified that error appears in the above-identified patent and that said Letters Patent is hereby corrected as shown below:

On the Title Page

On page 2, in Column 2, item (56) under "Other Publications", Line 14, delete "27," and insert --28,-- therefor In the Claims In Column 11, Line 42, in Claim 10, after "into", delete "to"

In Column 12, Line 43, in Claim 24, delete "hand" and insert --band-- therefor

Signed and Sealed this
Eleventh Day of June, 2019

Andrei Iancu
*Director of the United States Patent and Trademark Office*